United States Patent [19]

Bricker et al.

[11] Patent Number: 5,447,844

[45] Date of Patent: Sep. 5, 1995

[54] DIAGNOSTIC ASSAY FOR BACTERIA BASED ON FRAGMENT AMPLIFICATION USING INSERTION SEQUENCE LOCATION

[75] Inventors: Betsy J. Bricker; Shirley M. Halling, both of Ames, Iowa

[73] Assignee: The United States of America as represented by the Secretary of Agriculture, Washington, D.C.

[21] Appl. No.: 998,636

[22] Filed: Dec. 30, 1992

Related U.S. Application Data

[63] Continuation of Ser. No. 670,602, Mar. 14, 1991, abandoned.

[51] Int. Cl.$^6$ .......................... C12Q 1/68; C12P 19/34
[52] U.S. Cl. ....................................... 435/6; 435/91.2; 935/77; 935/78
[58] Field of Search ............................ 435/6, 91, 91.2; 935/77, 78

[56] References Cited

FOREIGN PATENT DOCUMENTS 0252558 1/1988 European Pat. Off. ................. 435/6

OTHER PUBLICATIONS

D. Thierry et al., "IS6110, An IS-Like Element of *Mycobacterium tuberculosis* Complex," Nucl. Acids Res. 18(1): 188 (1990).
P. H. Vary et al., "Use of Highly Specific DNA Probes and the Polymerase Chain Reaction to Detect *Mycobacterium paratuberculosis* in Johne's Disease," J. Clin. Microbiol. 28(5): 933–937 (May 1990).
Shirley M. Halling et al., "DNA Polymorphism and Repetitive DNA in Brucella," Abstract, 42nd Annual Brucellosis Research Conference, Nov. 4–5, 1989.
Shirley M. Halling et al., "A Highly Repeated DNA Sequence and DNA Polymorphism in *Brucella ovis*," Abstract H-248, 90th Annual Meeting of American Society for Microbiology, May 13–17, 1990, Anaheim, Calif.
Shirley M. Halling et al., "Polymorphism in Brucella spp. Due to Highly Repeated DNA," J. Bacteriol. 172(12): 6637–6640 (Dec. 1990).
Fred M. Tatum et al., "Nucleotide Sequence of an Insertional Element in *Brucella ovis*," Abstract H-36, 90th Annual Meeting of American Society for Microbiology, May 13–17, 1990, Anaheim, Calif.
Betsy J. Bricker et al., "Analysis of a Repeated DNA Element in Brucella Species," Abstract H-247, 90th Annual Meeting of American Society for Microbiology, May 13–17, 1990, Anaheim, Calif.

Primary Examiner—Stephanie W. Zitomer
Attorney, Agent, or Firm—M. Howard Silverstein; Curtis P. Ribando; John D. Fado

[57] ABSTRACT

A diagnostic assay is provided for identifying closely-related strains or species of bacteria which possess common insertion sequence which is present in different positions within the genomic or plasmidic DNA for the different strains or species. A fragment of DNA defined by a site within the insertion sequence and another site outside the insertion sequence is amplified, such as by polymerase chain reaction. By appropriately preselecting a different size fragment to be amplified in each of the candidate organisms, those organisms which are actually present in a biological sample can be positively identified by size of the amplified fragments.

10 Claims, 1 Drawing Sheet

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 848
        ( B ) TYPE: nucleic acid
        ( C ) STRANDEDNESS: double
        ( D ) TOPOLOGY: linear ( i i ) MOLECULE TYPE: genomic DNA ( x i ) SEQUENCE DESCRIPTION: SEQ ID NO:1:

| | | | | | |
|---|---|---|---|---|---|
| CTAGGGCGTG | TCTGCATTCA | ACGTAACCAG | ATCATAGCGC | ATGCGAGATG | 50 |
| GACGAAGCCC | ATGAATGCGG | TCAATGTTTT | CTCGCATCGC | AGCGCAATAC | 100 |
| GACGATAGCG | TTTCAACTTG | TTAAAAAGC | ATTCAATCTG | ATGGCGTTCC | 150 |
| TTGTACAGCC | TCCAGTCGAT | TGTTGGGACA | CTGGAACGTG | TTGGATTGAC | 200 |
| CTTGATCTGA | GCCGTTGCCT | TGAGATTGCT | GGCAATGAAG | GCCCTTAAGT | 250 |
| GATCGGCATC | ATAGGCTGCA | TCAGCAATGA | CATGCCCAC | ACCCTTCAAG | 300 |
| CCGGATAGAA | GGCTTGAAGC | TTGCGGACAG | TCACCATAAT | GGCCGGGTGT | 350 |
| TGGCTTTATT | CGCAGCGGTA | GGCCGATAGC | ATCGACAACA | GCATGCAGCT | 400 |
| TGGTCGTCAA | TCCACCGCGC | GAGCGACCGA | TGCAGGCAGC | TTCAGCCCCC | 450 |
| CTTTTGCGCC | CGCCGCATCT | GCGTGGACTT | TCGATATGGT | GCTATCAATG | 500 |
| AGGACATATT | CAAAGTCCGG | CGTATCAGCC | AGGGCATGGA | AAAGCCTTTC | 550 |
| CCATACACCG | GCGTGCGACC | AGCGCCGAAA | GCGGGCATGA | ACCGCTGTCC | 600 |
| ATTTGCCGAA | GGTCGCAGGC | AGATCGCGCC | AGTGCGCTGC | ATTGGCAGCC | 650 |
| ATCCACAAGA | TGGCGTCGAC | AAATAATCGG | TTATCAACGC | CACTGCGGCC | 700 |
| GGGCGTACCA | ACTCGCCCCG | GAAGATATGC | TTCGATCCGG | TTCCATTGCT | 750 |
| CATCTGTAAG | GCTTCGTCTG | CTCACGGCTG | TTCTCCTTTA | ACAACCTTGA | 800 |
| ATCAGAATTT | CGTACAAAAG | GGAATCCTTG | AATGCAGACA | AGCCCTAG | 848 |

( 2 ) INFORMATION FOR SEQ. ID NO. 2

( x i ) SEQUENCE DESCRIPTION: SEQ ID NO:2:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO:2:

TGGGCTTCGT    CCATCTCGCA    T        21

( 2 ) INFORMATION FOR SEQ ID NO:3:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO:3:

GTCATTGCTG    ATGCAGCCTA    T        21

(2) INFORMATION FOR SEQ ID NO:4:

(i) SEQUENCE CHARACTERISTICS:
        (A) LENGTH: 21
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO:4:

CGGGTTCTGG CACCATCGTC G      21

(2) INFORMATION FOR SEQ ID NO:5:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO:5:

TTTTCCAATC CCATCGTTTC CG      22

DIAGNOSTIC ASSAY FOR BACTERIA BASED ON FRAGMENT AMPLIFICATION USING INSERTION SEQUENCE LOCATION

This application is a continuation of application Ser. No. 07/670,602, filed Mar. 14, 1991 which is now abandoned.

BACKGROUND OF THE INVENTION

1. Field of the Invention

This invention relates to a diagnostic assay for distinguishing closely related bacterial strains or species from one another. The assay takes advantage of the presence of highly conserved insertional elements which are uniquely located in the genomic or plasmid DNA of a given strain or species.

2. Description of the Prior Art

The bacterial genus Brucella has been identified as the causative agent of a number of diseases in humans and animals. It is responsive for economically important diseases in cattle and other livestock. Perhaps the most noteworthy of such diseases is bovine brucellosis, which is asssociated with abortions and infertility in cattle. This disease is caused by the gram-negative organism, B. abortus. Symptoms of equine brucellosis, also caused by B. abortus, include abortions and swelling or abscesses that form at the withers and poll. In swine, B. suis causes abortions in sows and is responsible for orchitis in boars. In goats, B. melitensis is frequently shed in the milk and thereby transmitted to humans. In sheep, B. ovis is responsible for ram epididymitis in males and occasional abortions in females. Other species of Brucella include B. neotomae (isolated from the desert wood rat) and B. canis, found in dogs. The taxonomy of Brucella also accounts for eight recognized biotypes (biovars) of B. abortus plus the vaccine strain B. abortus S19. There are also five biotypes of B. suis and three biotypes of B. melitensis.

Identification of an organism as belonging to the genus Brucella can be accomplished by observation of growth characteristics in combination with serological and bacteriological methods. Typing of the organism to establish species and biovar is determined by host range, susceptibility to lysis by phages, and by oxidative metabolic profiles. It was reported by Allardet-Servent et al. [J. Bacteriol. vol. 170:4603–4607 (1988)] that electrophoretic profiles of total genomic DNA reveal species-specific DNA fingerprints for B. abortus, B. melitensis, and B. suis, and that DNA fingerprints of B. ovis separated this species from all others. Ficht et al. [Advances in Brucellosis Research, pages 36–51 (1990)] report that RFLPs in Brucella chromosomal DNA at the omp 2 porin gene locus can be used to distinguish two classes of B. abortus.

In recent years bacterial genomes and plasmids have been reported to contain insertion sequences (ISs). The bacterial sources of many such ISs are given in Galas et al. [Mobile DNA, ed. Douglas E. Berg and Martha M. Howe, American Society for Microbiology, Washington, D.C., pages 109–115 (1989)]. ISs are highly specialized genetic elements which are transposable and have a highly variable genetic map location, even within populations of the same bacterial species [Brahma et al., J. Gen. Micro., vol. 128:2229–22234 (1982); Hartl et al., Philos. Trans. R. Soc. London B. Bio. Sci., vol. 312:191–204 (1986)]. They are typically from 0.75 to 2.5 kilobase pairs in length and are usually flanked by short perfect or nearly perfect inverted repeat sequences between 15 and 25 base pairs (bp) long. They can have a copy number in bacterial genomes of up to a few hundred per genome. ISs cause insertion mutations and other chromosomal rearrangements. Most ISs have one long open reading frame encoding a transposase. IS1, the smallest active transposable element known to exist in prokaryotes, relies upon an alternative mechanism for transposition; namely, the expression of a fusion protein that has IS1 transposase activity by frameshifting [Proc. Natl. Acad. Sci. USA, vol. 86:4609–4613 (1989)].

Thierry et al. [Nucleic Acids Research, vol. 18:188 (1990)] report that insertional sequences have been found in most mycobacteria which have been examined, and these elements are useful as taxonomic markers. Vary et al. [J. Clin. Micro., vol. 28: 933–937 (1990)] report that DNA probes which hybridize to a mycobacterial insertion sequence, IS900, were highly specific for Mycobacterium paratuberculosis. Vary et al., supra, also report on the use of DNA sequences derived from IS900 to prepare DNA primers for detection and identification of M. paratuberculosis by the polymerase chain reaction (PCR).

SUMMARY OF THE INVENTION

Figure 1:
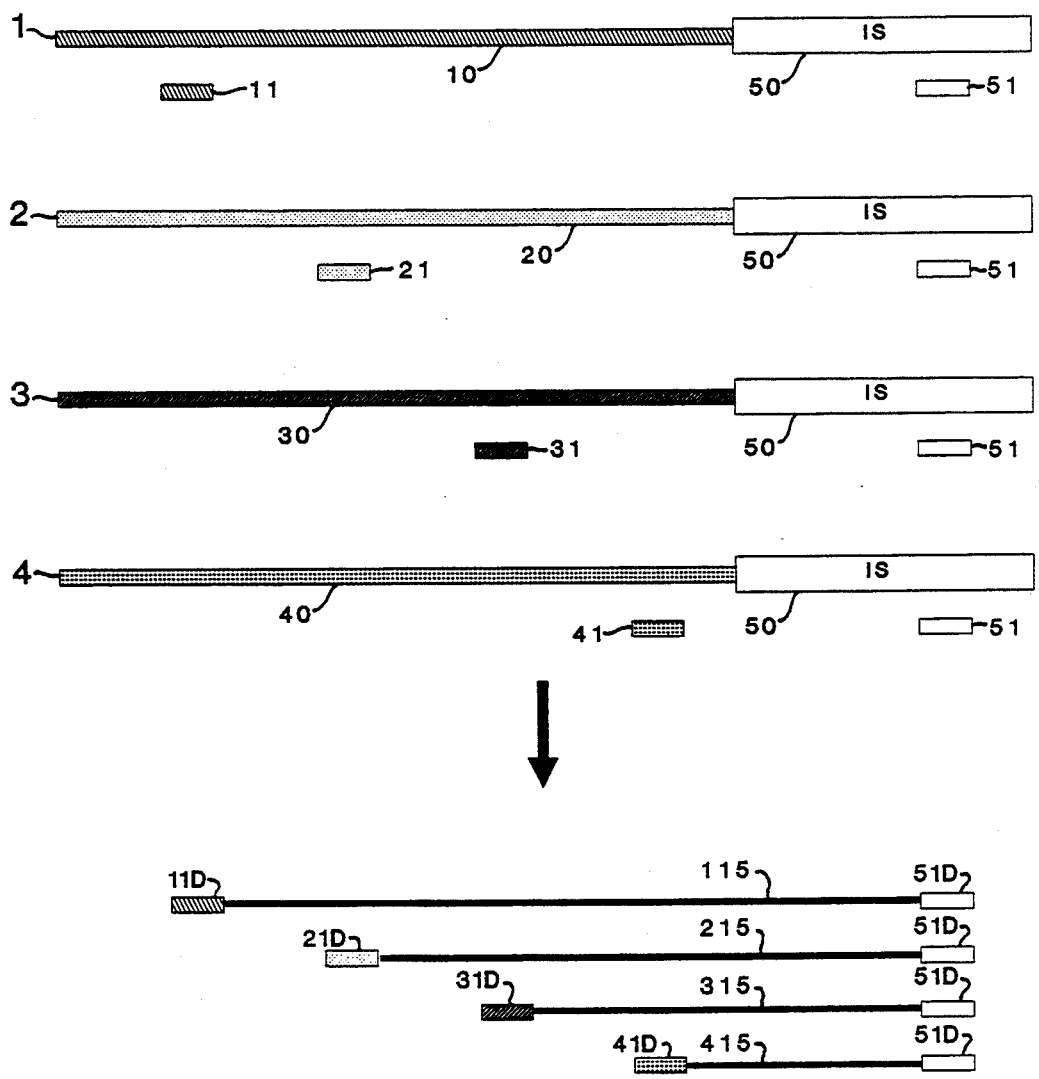
FIG. 1 diagrammatically depicts the strategy for amplifying regions of genomic DNA in related organisms in accordance with the invention.

We have now discovered that substantially stable ISs which are common to the DNA of related bacteria are often uniquely positioned within the genomic or plasmidic DNA of a given strain or species. This phenomenon lends itself to the development of a diagnostic assay for distinguishing closely related organisms from one another. By amplifying identifiable strain-specific or species-specific regions of DNA extending from a site within the insertional element to a site in a flanking sequence, the strain or species can be positively identified. This technique is particularly useful for identifying bacteria in biological samples. We have demonstrated utility of such an assay for strains of Brucella.

In accordance with this discovery, it is an object of the invention to provide a rapid and facile diagnostic assay for closely related strains or species of organisms, a particular advantage of such an assay being that it is unaffected by contamination by unrelated organisms.

It is another object of the invention to provide an assay as previously described which can be conducted on a small biological sample.

A further object of the invention is to provide our assay which can be conducted on living or dead cells so that, in the latter case, the risk of human infection by pathogens present in the test sample can be minimized.

Still another object of the invention is to provide a diagnostic assay which lends itself to automation and which can be conducted at low cost.

It is also an object of the invention to provide a diagnostic assay which can be conducted simultaneously for two or more closely related organisms which may be present together in the same biological sample.

Other objects and advantages of this invention will become readily apparent from the ensuing description.

DETAILED DESCRIPTION OF THE INVENTION

The basis of the invention is that a strain or species of bacteria can be identified as being distinct from other closely related strains or species of bacteria by virtue of the position in the chromosomal or plasmidic DNA of a substantially stable insertion sequence which is common to the members of a related group of bacteria. The terms "insertion sequence" ("IS") and "insertion element" are considered herein to be synonymous. An IS is defined herein as a small mobile genetic element, containing only genes related to insertion functions. ISs are typically characterized by a length of about .75–2.5 kb and ends comprising inverted repeats. The term "group" is used herein in the broadest sense to refer to any grouping of bacteria which share a common IS. A common IS is one in which the nucleotide sequences are highly conserved from one IS to the other; that is, wherein there are in each IS one or more regions of nucleotides have from about 15–30 bp which are 100%, or approximately 100%, homologous. The term "substantially stable" is intended to mean that the loss of the IS within the DNA of a population of bacteria would be a sufficiently infrequent event so as to pose little threat to the reliability of the assay.

As previously discussed, ISs have been identified in many genera of bacteria, and are thought to exist in most bacteria. The invention is applicable to those bacteria which share a common IS. In our work with Brucella, we have found that genome will contain a minimum of 5, and perhaps more than 20, copies of an IS per genome. We have also found that, except for perhaps $B.$ $canis$, all species of Brucella share a common IS, and at least one copy of the IS will be at a unique site in the genome of a given species. Thus for each species, there is at least one copy of the IS which is flanked by different sequences than those found flanking the IS copies in the other species. This heterology permits the selection of a signature region extending from the IS into the flanking sequence for use in identifying a given bacterium.

As previously mentioned, taxonomic identification is accomplished by amplifying the signature region and assaying for its presence. In the preferred embodiment of the invention, the amplification is conducted by polymerase of double-stranded DNA. However, the double-stranded DNA can be derived from single-stranded DNA or from RNA. In accordance with this procedure, a short stretch of each end of the signature region must first be sequenced. One end of the signature region is within the IS, and the other is within the flanking sequence. A first single-stranded oligonucleotide primer is selected so as to have base pair complementarity with a site at the end of the signature region within the IS on one of the strands of the double-stranded DNA. A second single-stranded primer is selected so as to have base pair complementarity with a site at the end of the signature region within the flanking sequence on the complementary strand of the DNA. When there is more than one candidate organism to be identified in the biological sample to be assayed, the first primer serves to initiate DNA synthesis within the IS for all such organisms. This is because it is assumed that all candidate organisms to be distinguished from one another share a common IS. However, a unique second primer is required for initiating DNA synthesis within each organism's flanking sequence. To the extent possible, primers should be selected so as to minimize base pairing with alternative sites, especially at the 3' end of the primer. Of course, a primer should not be self-complimentary (palindromic), nor should it be able to dimerize with itself or with other primers used in the reaction mixture. For reasons which will become apparent from the ensuing description, all the primers used in a given PCR assay should have similar annealing characteristics. Higher annealing temperatures are preferable, resulting in less nonspecific hybridization. The primers consist of approximately 15–30 bp, and preferably 18–25 bp. Primers rich in C and G can be shorter without reduction in the annealing temperature. Selection of appropriate primers can be assisted by application of commercial software programs designed for this purpose.

The most logical method for identifying one strain or species from another in a diagnostic assay is by the relative size of the amplified DNA fragment corresponding to the unique region. Thus the primer in the flanking region of each candidate organism is preselected to yield an amplified fragment of unique size which can be readily identified by comparison to a standard in gel electrophoresis or the like. The practical limitations of PCR would dictate that the amplified regions range in size from about 250 bp to about 3500 bp. The second primers, that is, those within the flanking sequences, are selected accordingly.

The basis of the strategy described above is illustrated diagrammatically in FIG. 1. Numerals 1–4 represent corresponding fragments of double-stranded DNA in related bacteria relative to a common IS, 50 . Sequences 10, 20, 30, and 40 are different from one another by virtue of the common IS being located in a different part of the DNA for each bacterial member. Primer 51 is complementary to a site within the IS on one of the strands of the denatured DNA. Both the primer ad the site are the same for each of the fragments 1–4. Primers 11, 21, 31, and 41 are complementary to unique sites in the respective fragments 1, 2, 3, and 4 on the strand of denatured DNA complementary to that containing the IS site. Repetitive cycles of PCR yield amplified regions 115, 215, 315, and 415 of double-stranded DNA. Sequences 11D, 21D, 31D, and 41D are the sequences corresponding to the unique primers, and 51D is the sequence corresponding to the IS primer.

Though the technique for conducting PCR is well-established in the literature, a brief description will be given. The preparation of template DNA to be assayed may range from simply washing the bacterial cells to CsCl-purification of the DNA, provided that non-DNA material present in the sample does not substantially interfere with the polymerase reaction or subsequent analysis.

PCR is conducted in a reaction mixture comprising a suitable buffer, such as 10 mM Tris-HCl, pH 8.3, 50 mM KCl, 1.5 mM $M_2Cl_2$, 0.001% wt/vol gelatin. The reaction mixture also comprises the template DNA, the DNA polymerase, the preselected primers as described above, and an ample amount of each of the four deoxynucleoside triphosphates (dATP, dCTP, dGTP, and TTP). The amount of polymerase must be sufficient to promote DNA synthesis throughout the predetermined number of amplification cycles. Guidelines as to the actual amount of polymerase are generally provided by the supplier of the PCR reagents and are otherwise readily determinable by a person of ordinary skill in the art. The amount of each primer must be in substantial excess of the amount of target DNA to be amplified.

The amount of primer needed for the reaction mixture can be estimated in terms of the ultimate number of amplified fragments desired at the conclusion of the reaction.

The reaction mixture is preferably overlaid with a mineral oil or the like for the purpose of preventing evaporation of the medium and undesired increases in the concentrations of the reagents during the course of the reaction. The first step of the reaction involves heating the mixture to melt the DNA; that is, to denature double-stranded configuration to two single-stranded templates. Using as an example Taq polymerase, the denaturing is typically conducted at a temperature in the range of about 90°–96° C. for about 1–2 min. The second step of the cycle is a cooling to about 35°–65° C., and preferably 50°–60° C., for about 1–3 min to permit annealing of the primers to the template. In the third step, the mixture is held within the temperature range of about 70°–75° C. for about 2–4 min to allow for primer extension by the polymerase. This cycle is usually repeated 20–35 times in order to achieve the desired amplification of the target sequence. Eventually amplification reaches a plateau as the proportion of reagents to products diminishes. Of course it is understood that the conditions set forth herein are merely exemplary, and optimization of the conditions for any given PCR would be within the purview of the person in the art. Additional detail regarding PCR is given by Arnhelm et al. [C&EN, pages 36–47 (Oct. 1, 1990)], herein incorporated by reference.

As previously mentioned, the amplified fragments are conveniently visualized by gel electrophoresis in comparison to preestablished standards. For each uniquely-sized region of bacterial DNA flanking the IS in the biological sample, a correspondingly unique band will be present in the gel, provided that the appropriate primers were supplied in the reaction mixture.

The invention is further illustrated by the following examples.

EXAMPLE 1

Cloning of the Unique Brucella Target Sites

DNA from each of *B. abortus* strain 2308, *B. canis* strain ATCC 23365, *B. melitensis* strain M16, *B. neotomae* strain SE-1169, *B. ovis* strain ANH 3572, and *B. suis* strain 1330 was cut with either HindIII, ClaI, or EcoRI. The fragments were separated on an agarose gel, blotted onto nylon membrane and probed by hybridization with DNA amplified from the IS. A unique fragment containing a copy of the IS was identified for each species. A plasmid library of each species was made by cutting the total DNA with one of the above enzymes and cloning the fragments into the multiple cloning site of pUC12. The *E. coli* cell line XL1-Blue (stratagene) was transformed with the plasmid library and plated for screening. Screening was done by filter hybridization of colonies (In Vitrogen newsletter "The Digest", vol. 2, Issue 4, Jan. 1990, pages 1–2) using the amplified IS sequence as probe. Clones positive for the IS element were isolated. The unique IS copy was identified by size of insert and by Southern hybridization to restriction enzyme-cut total Brucella DNA.

Sequencing of the IS

A DNA insertion of 840–848 bp (depending on whether CTAG at the start and end is a part of the inverted repeat or a duplication of the target site) was identified as an IS in the region of the *B. ovis* genome which hybridizes [Halling et al., J. Bacterial., vol. 172:6637–6640 (1990)] to the DNA sequences encoding BCSP31, a salt extractable protein of 31,00 daltons [Mayfield et al., Gene, vol. 63:1–9 (1988)] of *B. abortus*. The IS is cloned, pBA31-1I [Halling et al., supra] and has been subcloned for sequencing. The sequence of the IS was determined by the dideoxy method using a commercial kit marketed under the tradename "Sequenase Version 2.0" (U.S. Biochem Corp.) utilizing the double-stranded DNA protocol with $^{32}$P-dATP as label and either vector primers or synthetic primers complementary to the IS sequence. The IS sequence is given in the Sequence Listing as SEQ ID NO 1.

An IS was similarly isolated from *B. suis* and approximately 95% of it has been sequenced. Of that portion which has been sequenced, there is 98% homology with the IS from *B. ovis*.

Sequencing of Flanking DNA

The plasmid DNA from the selected clones was purified by either: (1) banding of DNA in a CsCl gradient, or (2) on a "Qiagen" chromatography column by the manufacturer's protocol. A sequence from inside the IS was used as the sequencing primer (5' TGG-GCT-TCG-TCC-ATC-TCG-CAT 3'; SEQ ID NO 2). The adjacent DNA was sequenced by the dideoxy method described above for sequencing the IS.

Using the sequence data determined in Example 1 for the IS from *B. ovis* and sequence data derived from the region flanking the IS, primers for use in the PCR were selected as follows. Since the length of product is important, a specific region of the sequence a predetermined distance from the start of the IS was identified for the primer search. Primers 21–23 bp in length were chosen primarily on the basis of a high GC content (indicative of a high annealing temperature). Selected primers were then checked for self-complementary regions (palindromes), dimer formation with self, and dimer formation with the other primer(s). The first primer in a given region to meet all criteria was synthesized as above, purified on HPLC, and dried. The following primers were constructed for use in Examples 2–8:

| Primers | |
| --- | --- |
| IS-specific primer: | 5' GTC-ATT-GCT-GAT-GCA-GCC-TAT 3' (SEQ ID NO. 3) |
| *B. ovis*-specific primer: | 5' CGG-GTT-CTG-GCA-CCA-TCG-TCG 3' (SEQ ID NO. 4) |
| *B. abortus*-spec. primer: | 5' TTT-TCC-AAT-CCC-ATC-GTT-TCC-G 3' (SEQ ID NO. 5) |

EXAMPLE 2

PCR of Six Brucella Species Using *B. ovis*-Specific Primers

Genomic DNAs were isolated from the following organisms for use as putative template DNA:

Templates:
- *B. abortus* strain 2308
- *B. canis* strain ATCC 23365
- *B. melitensis* strain M16
- *B. neotomae* strain SE-1169
- *B. ovis* strain ANH 3572
- *B. suis* strain 1330

The DNAs were isolated from methanol-killed cells essentially as described by Anderson et al. [J. Bacteriol. 160:748–754 (1984)], except that the cells were incubated in the presence of "Zwittergent 3-14" (1%) and citric acid (0.1 M) at 50° for 1 hr before being lysed. Briefly, detergent-treated cells were washed and then lysed by sequential addition of lysozyme, proteinase K, EDTA, and sarcosine. The lysate was treated with RNase A, extracted with phenol, precipitated from ethanol, dissolved in TE [10 mM Tris hydrochloride, 1 mM disodium EDTA (pH 8.0)], and centrifuged in the presence of CsCl.

Each of the above genomic templates were individually subjected to PCR in the presence of the IS-specific and B. ovis-specific primers in accord with the following procedure.

| Primers: | |
|---|---|
| IS-specific primer: | 5' GTC-ATT-GCT-GAT-GCA-GCC-TAT 3' (SEQ ID NO. 3) |
| B. ovis-specific primer: | 5' CGG-GTT-CTG-GCA-CCA-TCG-TCG 3' (SEQ ID NO. 4) |

A master mix was prepared exclusive of primers and templates comprising the following components:

| Component | Stock concentrations | Volume added |
|---|---|---|
| H₂O | ... | 615 μl |
| dATP | 10 mM | 20 μl |
| dCTP | 10 mM | 20 μl |
| dGTP | 10 mM | 20 μl |
| dTTP | 10 mM | 20 μl |
| rxt buffer | * | 100 μl |
| Taq polymerase | 5 units/μl | 5 μl |

*100 mM Tris-HCl, pH 8.3; 500 mM KCl; 15 mM MgCl₂; 0.01% wt/vol gelatin.

A 40-μl aliquot of master mix was dispensed into a "Gene Amp" 500 μl plastic tube and stored at −20° C. until used. At the time of use, the tube was thawed, and the contents were combined with 0.5 μl of a 20-μM stock solution of each of the IS-specific and the B. ovis-specific primers together with 1 μl (one unit) of a priming specificity enhancer ("Perfect Match" by Stratagene), 5 μl (5 ng) of template and 3 μl water. The reaction mixture was overlaid with 50 μl mineral oil.

The tube containing the reaction mixture was placed in a Techne PHC-1 Thermocycler. The thermocycling conditions were 1.2 min at 92° C. to melt (denature) the DNA, 2.0 min at 55° C. (to anneal the primers to the template) and 3 min at 72° C. (to synthesize the DNA). The mixture was passed through 35 cycles.

The amplified fragment of DNA was analyzed by gel electrophoresis. A sample of 4 μl of each PCR reaction mix was added to 5 μl loading dye (final conc.: 5% glycerol, 0.5% EDTA, 2 mM Tris, pH 8.0, 0.01% xylene cyanole and 0.01% bromophenol blue) and the entire 9 μl of solution was loaded on a 1.2% agarose gel. The gel was processed at 70 V for 1.33 hr in 0.5X TBE [TBE=tris-borate-EDTA (Maniatis)] buffer. The DNA was stained 10–30 min with ethidium bromide solution (0.25 mg/500 ml in 0.5X TBE) and then visualized on an ultraviolet light box for photography.

Based upon sequence data, it was expected that an amplified fragment of B. ovis including the primers would be approximately 1001 bp. A band indicating the presence of an amplified fragment was obtained only for the sample containing the B. ovis template. The observed size of the fragment from the gel electrophoresis was within the range of 1000–1100 bp, confirming that the region defined by the primers was unique to B. ovis.

EXAMPLE 3

The procedure of Example 2 was repeated, substituting a B. abortus-specific primer for the B. ovis-specific primer:

| Primers: | |
|---|---|
| IS-specific primer: | 5' GTC-ATT-GCT-GAT-GCA-GCC-TAT 3' (SEQ ID NO. 3) |
| B. abortus-spec. primer: | 5' TTT-TCC-AAT-CCC-ATC-GTT-TCC-G 3' (SEQ ID NO. 5) |

The slightly modified procedure for individually subjecting each of the above genomic templates to PCR in the presence of the IS-specific and B. abortus-specific primers was as follows. A 40-μl aliquot of master mix in a "Gene Amp" 500 μl plastic tube was combined with 2.5 μl of a 20-μM stock solution of each of the IS-specific and the B. abortus-specific primers together with 5 μl mineral oil.

The tube containing the reaction mixture was placed in a Techne PHC-1 Thermocycler. The thermocycling conditions were 1.2 min at 92° C., 2.0 min at 55° C., and 3 min at 72° C. The mixture was passed through 35 cycles.

The amplified fragments of DNA were analyzed by gel electrophoresis. A sample of 5 μl of each PCR reaction mix was added to 5 μl loading dye (final conc.: 5% glycerol, 0.5% EDTA, 2 mM Tris, pH 8.0, 0.01% xylene cyanole and 0.01% bromophenol blue) and the entire 10 μl of solution was loaded on a 1.2% agarose gel. The gel was processed at 70 V for 2 hr in 1X TBE buffer. The DNA was stained 10–30 min with ethidium bromide solution (0.25 mg/500 ml in 0.5X TBE) and then visualized on an ultraviolet light box for photography.

Based upon sequence data, it was expected that an amplified fragment of B. abortus including the primers would be approximately 508 bp. A band indicating the presence of an amplified fragment was obtained only for the sample containing the B. abortus template. The observed size of the fragment from the gel electrophoresis was within the range of 505–575 bp, confirming that the region defined by the primers was unique to B. abortus.

EXAMPLE 4

The procedure of Example 2 was substantially repeated, using various combinations of primers and templates. In some cases both B. ovis-specific primer and B. abortus-specific primer were used together with the IS-specific primer. The templates were genomic DNAs purified on CsCl gradients as in Example 2.

| Primers: | |
|---|---|
| P1 = IS-specific primer: | 5' GTC-ATT-GCT-GAT-GCA-GCC-TAT 3' (SEQ ID NO. 3) |
| P2 = B. ovis-specific primer: | 5' CGG-GTT-CTG-GCA-CCA-TCG-TCG 3' (SEQ ID NO. 4) |
| P3 = B. abortus-spec. primer: | 5' TTT-TCC-AAT-CCC-ATC-GTT-TCC 3' (SEQ ID NO. 5) |

Templates:
 Ab=B. abortus strain 2308
 OV=B. ovis strain ANH 3572
 Su=B. suis strain 1330

The procedure for conducting the PCR was as follows. A 40 μl aliquot of master mix in a "Gene Amp"

500 μl plastic tube was combined with 5 μl (5 ng) of each template, 2.5 μl of a 20-μM stock solution of each primer. The reaction mixture was overlaid with 50 μl mineral oil.

The tube containing the reaction mixture was placed in a Techne PHC-1 thermocycler. The thermocycling conditions were 1.2 min at 92° C., 2.0 min at 55° C. and 3 min at 72° C. The mixture was passed through 35 cycles.

The amplified fragments of DNA were analyzed by gel electrophoresis. A sample of 5 μl of each PCR reaction mix was added to 5 μl loading dye (final conc.: 5% glycerol, 0.5% EDTA, 2 mM Tris, pH 8.0, 0.01% xylene cyanole, and 0.01% bromophenol blue) and the entire 10 μl of solution was loaded on a 1% agarose gel. The gel was processed at 80 V for 1 hr in 0.5X TBE buffer. The DNA was stained 10-30 min with ethidium bromide solution (0.25 mg/500 ml in 0.5X TBE) and then visualized on an ultraviolet light box for photography.

Based upon sequence data, it was expected that an amplified fragment of *B. ovis* including the primers would be approximately 1001 bp. and that an amplified fragment of *B. abortus* including the primers would be approximately 508 bp. Bands indicating the presence of amplified fragments were obtained only for the sample containing the *B. ovis* and/or the *B. abortus* templates. The observed sizes of the fragments from the gel electrophoresis were within the range of 990–1100 bp for the *B. ovis* and 490–550 bp for the *B. abortus*, confirming that the regions defined by the primers in combination with the IS primer are unique to each of the respective organisms. The results of the electrophoresis are summarized in Table I, below.

TABLE I

PCR with Mixed Primers and Templates

| Lane | Primers | Templates | Bands Ab | Bands Ov | Bands Su |
|---|---|---|---|---|---|
| 1 | MW stds. | N/A | N/A | N/A | N/A |
| 2 | P1 + P2 + P3 | Ab | + | − | − |
| 3 | P1 + P2 + P3 | Ov | − | + | − |
| 4 | P1 + P2 + P3 | Ab + Ov | + | + | − |
| 5 | P1 + P2 + P3 | Ab + Ov + Su | + | + | − |
| 6 | P1 + P3 | Ab + Ov | − | + | − |
| 7 | P1 + P3 | Ov + Su | − | + | − |

EXAMPLE 5

The procedure of Example 3 was repeated with the addition of plasmidic DNA as a template. The plasmid was p1D1 which contains the left HindIII fragment of the *B. abortus*-specific IS copy and adjacent DNA.

| Primers: | |
|---|---|
| IS-specific primer: | 5' GTC-ATT-GCT-GAT-GCA-GCC-TAT 3' (SEQ ID NO. 3) |
| *B. abortus*-spec. primer: | 5' TTT-TCC-AAT-CCC-ATC-GTT-TCC-G 3' (SEQ ID NO. 5) |

A 40 $\mu$l aliquot of master mix in a "Gene Amp" 500 $\mu$l plastic tube was combined with 2.5 $\mu$l of a 20 $\mu$M stock solution of each of the IS and the *B. abortus*-specific primer together with 5 $\mu$l (5 ng) of genomic template or 1 $\mu$l (1 ng) plasmid template. The reaction mixture was overlaid with 50 $\mu$l mineral oil.

The tube containing the reaction mixture was placed in a Techne PHC-1 Thermocycler. The thermocycling conditions for the first three cycles were 1.2 min at 96° C., 2.0 min at 55° C., and 3 min at 72° C. Thereafter, 35 cycles were run wherein the conditions were 1.2 min at 95° C., 2.0 min at 55° C., and 3 min at 72° C.

The amplified fragments of DNA were analyzed by gel electrophoresis. A sample of 5 $\mu$l of each PCR reaction mix was added to 5 $\mu$l loading dye (final conc.: 5% glycerol, 0.5% EDTA, 2 mM Tris, pH 8.0, 0.01% xylene cyanole and 0.01% bromophenol blue) and the entire 10 $\mu$l of solution was loaded on a 1.2% agarose gel. The gel was processed at 85 V for 1.66 hr in TBE buffer. The DNA was stained 15 min in ethidium bromide solution (0.25 mg/500 ml in 0.5X TBE). To increase separation, the electrophoresis was continued at 40 V for 2 hr. The DNA was then visualized on an ultraviolet light box for photography.

Bands indicating the presence of amplified fragments were obtained only for the samples containing the *B. abortus* genomic template and the *B. abortus* plasmidic template. The bands for these entities migrated to the same position in the gel, indicating that the amplified fragments were of identical size.

EXAMPLE 6

The procedure of Example 2 was substantially repeated, using a combination of the *B. ovis*-specific primer and *B. abortus*-specific primer together with the IS-specific primer. The templates were genomic DNAs obtained from 10 field isolates of *B. ovis* as shown in Table II.

| Primers: | |
|---|---|
| IS-specific primer: | 5' GTC-ATT-GCT-GAT-GCA-GCC-TAT 3' (SEQ ID NO. 3) |
| *B. ovis*-specific primer: | 5' CGG-GTT-CTG-GCA-CCA-TCG-TCG 3' (SEQ ID NO. 4) |
| *B. abortus*-spec. primer: | 5' TTT-TCC-AAT-CCC-ATC-GTT-TCC 3' (SEQ ID NO. 5) |

TABLE II

Strains of *B. ovis*

| No. | Strain | Geographic origin | Year Isolated |
|---|---|---|---|
| 1 | ANH3572 | Idaho | 1968 |
| 2 | 51-265 | New Zealand | 1957 |
| 3 | 53-287 | New Zealand | 1957 |
| 4 | 53-37 | New Zealand | 1957 |
| 5 | 1922 | California | 1965 |
| 6 | L-80-891 | Colorado | 1984 |
| 7 | L-745 | Colorado | 1984 |
| 8 | 21466 | Colorado | 1988 |
| 9 | 10546 | Colorado | 1986 |
| 10 | 12576 | Colorado | 1984 |

As indicated in Table II, the *B. ovis* isolates represent a significant cross-section of geographic origins and dates of isolation. Isolates 1–10 are being maintained in a private collection at the National Animal Disease Center, Ames, Iowa. These cultures were freeze dried after low passage and stored at low temperature. Isolates 5–10 were isolated from rams with epididymitis and were obtained from a collection at Colorado State University.

The cultures were grown beneath an atmosphere of $CO_2$ (5%) on tryptose agar supplemented with heat-inactivated calf serum (5%) and agar (0.5%). Several plates were streaked from a single colony and incubated for 3–4 days before cells were collected by suspension in sterile saline (0.85% NaCl). The isolates were then killed in 67% methanol and 33% saline.

The DNA was isolated and purified on CsCl gradients as in Example 2. All samples were diluted to 1 ng/μl in TE (10 mM Tris, 1 mM EDTA, pH8).

Vials were prepared containing 25μl master mix, 0.3 μl of a 20-μM stock solution of each of the 3 primers, and 0.5 μl (0.5 units) of "Perfect Match", supra. To each vial, 3 μl (3 ng) of the purified DNA was added. The reaction mixture was overlaid with 25 μl mineral oil. A sample of B. abortus whole cells isolated as described in Example 7, below, was prepared for PCR similar to the B. ovis DNA and was included as a control.

The tubes containing the reaction mixture were placed in a Techne PHC-1 Thermocycler initially heated to 94° C. for 1.2 min to inactivate DNAses and lyse the cells of the control. The samples were cycled through the program of 1.2 min at 92° C., 2.0 min at 55° C., and 3 min at 72° C. for 30 cycles. Immediately after the run, 3 μl of 0.5 mM EDTA was added to inhibit any surviving DNAse activity and the samples were refrigerated overnight.

The amplified fragments of DNA were analyzed by gel electrophoresis. A sample of 5 μl of each PCR reaction product was added to 5 μl loading dye (final conc.: 5% glycerol, 0.5% EDTA, 2 mM Tris, pH 8.0, 0.01% xylene cyanole, and 0.01% bromophenol blue) and the entire 10 μl of solution was loaded on a 1.2% agarose gel. The gel was processed at 70 V for 3.33 hr in 0.5X TBE buffer. The DNA was stained 10-30 min with ethidium bromide solution (0.25 mg/500 ml in 0.5X TBE) and then visualized on an ultraviolet light box for photography.

Bands indicating the presence of amplified B. ovis templates were obtained for all 10 B. ovis samples. For these same samples, there were no bands indicative of amplified B. abortus templates. The B. abortus control contained a B. abortus-specific band.

EXAMPLE 7

The procedure of Example 3 was repeated using whole cells from 23 field isolates of B. abortus in the PCR as the source of template DNA. These isolates were collected from scattered sources throughout the United States and were obtained from the USDA Diagnostic Bacteriology Laboratory in Ames, Iowa. These isolates are being maintained in a collection at the National Animal Disease Center, Ames, Iowa.

| Primers: | |
|---|---|
| P1 = IS-specific primer: | 5' GTC-ATT-GCT-GAT-GCA-GCC-TAT 3' (SEQ ID NO. 3) |
| P3 = B. abortus-spec. primer: | 5' TTT-TCC-AAT-CCC-ATC-GTT-TCC 3' (SEQ ID NO. 5) |

Two of the B. abortus isolates tested represented the vaccine strain S19. Nineteen of field isolates were biovar 1, and two were biovar 4. The isolates were grown on nutritive agar plates and then killed as described in Example 6 for the field isolates of B. ovis.

For each isolate, 10 microliters of cells (at $10^{7-9}$ cells/ml) were added to 500 μl water in a 500 μl "Gene Amp" microfuge tube and pelleted in microfuge to remove the methanol. Pellets were approximately 0.5 mm in diameter. The water was removed and replaced with 50 μl master mix containing 2.5 μl of a 20-μM stock solution of each of the IS primer and the B. abortus-specific primer. The pellet was resuspended in the master mix by tapping the tube. The reaction mixture was resuspended in the master mix by tapping the tube. The reaction mixture was overlaid with 50 μl mineral oil.

The tubes containing the reaction mixture were placed in a Techne PHC-1 Thermocycler initially heated to 94° C. for 1.2 min to inactivate DNAses and lyse the cells. The samples were cycled through the program of 1.2 min at 92° C., 2.0 min at 55° C., and 3 min at 72° C. for 30 cycles. Immediately after the run, 3 μl of 0.5 mM EDTA was added to inhibit any surviving DNAse activity and the samples were refrigerated overnight.

The amplified fragments of DNA were analyzed by gel electrophoresis. A sample of 5 μl of each PCR reaction product was added to 5 μl loading dye (final conc.: 5% glycerol, 0.5% EDTA, 2 mM Tris, pH 8.0, 0.01% xylene cyanole, and 0.01% bromophenol blue) and the entire 10 μl of solution was loaded on a 1.2% agarose gel. The gel was processed at 70 V for 1.33 hr in 0.5X TBE buffer. The DNA was stained 10-30 min with ethidium bromide solution (0.25 mg/500 ml in 0.5X TBE) and then visualized on an ultraviolet light box for photography.

Bands indicating the presence of amplified B. abortus templates were obtained for all 19 isolates.

EXAMPLE 8

The procedure of Example 7 was repeated with 7 additional field isolates of B. abortus, except that the reaction mixture comprised a cocktail of the IS-specific primer, the B. abortus-specific primer and the B. ovis-specific primer, all in amounts of 2.5 μl of a 20 μM stock solution.

| Primers: | |
|---|---|
| IS-specific primer: | 5' GTC-ATT-GCT-GAT-GCA-GCC-TAT 3' (SEQ ID NO. 3) |
| B. ovis-specific primer: | 5' CGG-GTT-CTG-GCA-CCA-TCG-TCG 3' (SEQ ID NO. 4) |
| B. abortus-spec. primer: | 5' TTT-TCC-AAT-CCC-ATC-GTT-TCC 3' (SEQ ID NO. 5) |

One of the B. abortus isolates tested represented the vaccine strain S19 and six of the isolates were biovar 1. In the gel electrophoresis, bands indicating the presence of amplified B. abortus templates were obtained for all 7 isolates.

It is understood that the foregoing detailed description is given merely by way of illustration and that modification and variations may be made therein without departing from the spirit and scope of the invention.

We claim:

1. A method for identifying in a biological sample an organism, which organism is a member of a group of organisms which share a common, substantially stable, insertion sequence and wherein the insertion sequence of said member is in a unique position on the DNA of the organism relative to that of the other members of the group, the method comprising the steps of:
    (a) amplifying a fragment of DNA from said organism, the endpoints of said fragment being defined by a first site within the insertion sequence and a second site outside the insertion sequence;
    (b) comparing the amplified fragment of DNA to a standard of DNA unique to said member and indicate of said fragment; and
    (c) identifying said organism based upon a correspondence of the amplified fragment with the standard.

2. The method of claim 1 wherein the comparing of step (b) is based upon the size of the fragment.

3. The method of claim 1 wherein said organism is a strain of Brucella.

4. The method of claim 1 wherein said organism is selected from the group consisting of *Brucella abortus, Brucella ovis, Brucella suis, Brucella melitensis, Brucella neotomae,* and *Brucella canis.*

5. The method of claim 1 wherein said amplifying is conducted by polymerase chain reaction.

6. The method of claim 5 wherein said DNA fragment is 250–3500 base pairs in length.

7. The method of claim 5 wherein a primer is provided complementary to each of said sites, and each primer is 15–30 bases in length.

8. The method of claim 7 wherein each of said primers is 19–25 bases in length.

9. The method of claim 1 wherein more than one member of said group of organisms is simultaneously identified.

10. A diagnostic kit useful for identifying at least one organism in a biological sample, which organism is a member of a group of organisms which share a common, substantially stable, insertion sequence and wherein the insertion sequence of said member is in a unique position on the DNA of the organism relative to that of the other members of the group, the kit comprising:
    a. a first primer complementary to a first site within the insertion sequence;
    b. for each related organism to be identified, a second primer complementary to a second site outside the insertion sequence, wherein each second primer is preselected so that the DNA region between the first and second primer for each organism is uniquely identifiable;
    c. a polymerase;
    d. dATP, dCTP, dGTP, and dTTP; and
    e. a reaction buffer.

* * * * *